United States Patent
Ko et al.

(10) Patent No.: US 9,144,387 B2
(45) Date of Patent: Sep. 29, 2015

(54) ELECTRODE FOR MEASURING BIO POTENTIAL, METHOD OF MANUFACTURING THE ELECTRODE, AND SYSTEM FOR MEASURING PHYSIOLOGICAL SIGNAL

(71) Applicant: Samsung Electronics Co., Ltd., Suwon-si (KR)

(72) Inventors: Byung-hoon Ko, Hwaseong-si (KR); Tak-hyung Lee, Seoul (KR); Youn-ho Kim, Hwaseong-si (KR); Kun-soo Shin, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 46 days.

(21) Appl. No.: 13/762,301

(22) Filed: Feb. 7, 2013

(65) Prior Publication Data
US 2013/0204110 A1    Aug. 8, 2013

(30) Foreign Application Priority Data
Feb. 7, 2012 (KR) .................. 10-2012-0012528

(51) Int. Cl.
| | |
|---|---|
| A61B 5/0408 | (2006.01) |
| A61B 5/0478 | (2006.01) |
| A61B 5/0488 | (2006.01) |
| A61B 5/04 | (2006.01) |
| H01R 43/16 | (2006.01) |
| A61B 5/00 | (2006.01) |

(Continued)

(52) U.S. Cl.
CPC .............. *A61B 5/04* (2013.01); *A61B 5/04087* (2013.01); *A61B 5/6832* (2013.01); *H01R 43/16* (2013.01); *A61B 5/0478* (2013.01); *A61B 5/0488* (2013.01); *A61B 5/0492* (2013.01); *A61B 5/0496* (2013.01); *A61B 5/0533* (2013.01); *A61B 2562/0209* (2013.01); *Y10T 29/4921* (2015.01)

(58) Field of Classification Search
CPC . A61B 5/04087; A61B 5/0478; A61B 5/0492
USPC .................................................. 600/391, 392
See application file for complete search history.

(56) References Cited

U.S. PATENT DOCUMENTS 3,774,592 A * 11/1973 Lahr .............................. 600/392
4,362,165 A * 12/1982 Carmon et al. ............... 600/396

(Continued)

FOREIGN PATENT DOCUMENTS

| KR | 10-2006-0058089 A | 5/2006 |
| KR | 10-0825888 B1 | 4/2008 |
| KR | 10-2010-0104404 A | 9/2010 |

*Primary Examiner* — Lee S Cohen
(74) *Attorney, Agent, or Firm* — NSIP Law

(57) ABSTRACT

An electrode for measuring a bio potential includes a conductive adhesive having one side configured to have at least two metal electrodes attached thereto while the electrode is being used, and another side configured to be attached to a living body while the electrode is being used, the conductive adhesive having a predetermined area and a predetermined thickness; and a supporting element configured to support the conductive adhesive while the conductive adhesive is attached to the living body; wherein an impedance is formed between the at least two metal electrodes while the at least two metal electrodes are attached to the side of the conductive adhesive, the impedance depending on a thickness of the conductive adhesive and having a value that prevents the at least two metal electrodes from being shorted together.

26 Claims, 13 Drawing Sheets

(51) Int. Cl.
　　*A61B 5/0492*　　(2006.01)
　　*A61B 5/0496*　　(2006.01)
　　*A61B 5/053*　　(2006.01)

(56) References Cited

U.S. PATENT DOCUMENTS

| | | | |
|---|---|---|---|
| 4,458,696 A * | 7/1984 | Larimore | 607/152 |
| 4,763,660 A * | 8/1988 | Kroll et al. | 600/391 |
| 4,827,939 A * | 5/1989 | Cartmell et al. | 600/392 |
| 5,024,227 A * | 6/1991 | Schmid | 600/391 |
| 5,511,553 A * | 4/1996 | Segalowitz | 600/508 |
| 5,678,545 A * | 10/1997 | Stratbucker | 607/152 |
| 5,824,033 A * | 10/1998 | Ferrari | 607/142 |
| 6,134,480 A * | 10/2000 | Minogue | 607/152 |
| 6,208,888 B1 | 3/2001 | Yonce | |
| 6,912,414 B2 | 6/2005 | Tong | |
| 8,788,009 B2 * | 7/2014 | Greene et al. | 600/372 |
| 2005/0143669 A1 * | 6/2005 | Matsumura et al. | 600/509 |
| 2006/0149146 A1 | 7/2006 | Schmidt et al. | |
| 2010/0016703 A1 * | 1/2010 | Batkin et al. | 600/392 |
| 2011/0137200 A1 | 6/2011 | Yin et al. | |

\* cited by examiner

ELECTRODE FOR MEASURING BIO POTENTIAL, METHOD OF MANUFACTURING THE ELECTRODE, AND SYSTEM FOR MEASURING PHYSIOLOGICAL SIGNAL

CROSS-REFERENCE TO RELATED APPLICATIONS

This application claims the benefit of Korean Patent Application No. 10-2012-0012528 filed on Feb. 7, 2012, in the Korean Intellectual Property Office, the disclosure of which is incorporated herein by reference in its entirety for all purposes.

BACKGROUND

1. Field

This disclosure relates to an electrode for measuring a bio potential, a method of manufacturing the electrode, and a system for measuring a physiological signal.

2. Description of Related Art

Recent healthcare systems improve accuracy and convenience of diagnosis by measuring various physiological signals in daily life. In particular, smart healthcare systems for providing health-related services through personal health information databases, helping medical staff to perform tele-diagnoses, and delivering results of diagnoses and prescriptions to patients are being introduced.

A human body is a conductor in which an electrical field is formed due to an action potential that is generated by electrical excitation of cells. Therefore, electrical characteristics of the internal part of a body may be measured by detecting a small amount of current or detecting a change in current with respect to external stimuli in the body.

Generally, various bio potentials, such as an electrocardiogram (ECG), an electromyogram (EMG), an electroencephalogram (EEG), galvanic skin resistance (GSR), electrooculography (EOG), body temperature, heartbeat, blood pressure, and body movement, may be measured by using such a principle, and an electrode for a living body is used to detect changes in such physiological signals.

FIG. 1 illustrates an example of an electrode for a living body attached to the skin of a user, and a portable measuring system. An electrode for a living body is a medium for connecting the skin of a user to a system for measuring a physiological signal (hereinafter, a physiological signal measuring system), and affects the quality of the measured physiological signals and user convenience. In daily life, in order for an electrode for a living body to be attached to the living body of a user and to measure physiological signals of the user all of the time, various technical problems with respect to accuracy of measurement, communication, power consumption, and the technical problems need to be resolved.

In order to always have a physiological signal measuring system on a living body in daily life, an area of an electrode that is in contact with the skin of the body needs to be minimized to reduce skin irritation. In addition, it is necessary to reduce motion artifacts to accurately measure physiological signals during exercise.

FIG. 2 illustrates an example of noise generated in a measured physiological signal due to a change in an interface caused by a movement of a body, and shows that a signal-to-noise ratio (SNR) of the measured physiological signal is reduced by the movement of the body.

SUMMARY

In one general aspect, an electrode for measuring a bio potential includes a conductive adhesive having one side configured to have at least two metal electrodes attached thereto while the electrode is being used, and another side configured to be attached to a living body while the electrode is being used, the conductive adhesive having a predetermined area and a predetermined thickness; and a supporting element configured to support the conductive adhesive while the conductive adhesive is attached to the living body; wherein an impedance is formed between the at least two metal electrodes while the at least two metal electrodes are attached to the side of the conductive adhesive, the impedance depending on a thickness of the conductive adhesive and having a value that prevents the at least two metal electrodes from being shorted together.

The electrode may further include an adhesion material coated on one side of the supporting element, the one side of the supporting element facing the living body while the conductive adhesive is attached to the living body, the adhesion material contacting the living body and adhering to the living body while the conductive adhesive is attached to the living body.

The impedance may further depend on a distance between points on the conductive adhesive where the at least two metal electrodes are attached to the conductive adhesive.

The impedance may further depend on areas of the at least two metal electrodes.

The impedance may further depend on a composition of the conductive adhesive.

Each of the at least two metal electrodes attached to the conductive adhesive may cooperate with the conductive adhesive to form an electrode having a filter characteristic that may function as a filter for an electrical signal sensed by the electrode having the filter characteristic.

The electrode may further include protective films attached to both sides of the conductive adhesive and the supporting element.

In another general aspect, an electrode for measuring a bio potential includes at least two metal electrodes; a conductive adhesive having one side to which the at least two metal electrodes are attached, and another side configured to be attached to a living body while the electrode is being used, the conductive adhesive having a predetermined area and a predetermined thickness; and a supporting element configured to support the conductive adhesive while the conductive adhesive is attached to the living body; wherein an impedance is formed between the at least two metal electrodes attached to the side of the conductive adhesive, the impedance depending on a thickness of the conductive adhesive and having a value that prevents the at least two metal electrodes from being shorted together.

The at least two metal electrodes may be configured to be directly connected to a physiological signal measuring system.

The electrode may further include at least two terminals respectively corresponding to the at least two metal electrodes and respectively connected to the at least two metal electrodes; and the at least two terminals may be configured to be connected to a physiological signal measuring system to connect the at least two metal electrodes to the physiological signal measuring system.

In another general aspect, a system for measuring a physiological signal includes at least two metal electrodes; an electrode for measuring a bio potential, the electrode including a conductive adhesive having one side to which the at least two metal electrodes are attached, and another side configured to be attached to a living body while the electrode is being used, the conductive adhesive having a predetermined area and a predetermined thickness; and a supporting element configured to support the conductive adhesive while the conductive adhesive is attached to the living body; the system further including an amplifier configured to amplify a difference between signals detected by two metal electrodes selected from the at least two metal electrodes to produce an amplified signal; and a processor configured to process the amplified signal; wherein an impedance is formed between the at least two metal electrodes attached to the side of the conductive adhesive, the impedance depending on a thickness of the conductive adhesive and having a value that prevents the at least two metal electrodes from being shorted together.

The system may further include a metal electrode selection unit configured to select the two metal electrodes from the at least two metal electrodes.

The processor may be further configured to process the amplified signal to obtain processed data by executing a predetermined program; and the system may further include a storage unit configured to store the predetermined program and the processed data; and a wireless transmission and reception unit configured to transmit the processed data to an external device.

In another general aspect, a system for measuring a physiological signal includes an electrode for measuring a bio potential, the electrode including at least two metal electrodes, a conductive adhesive having one side to which the at least two metal electrodes are attached, and another side configured to be attached to a living body while the electrode is being used, the conductive adhesive having a predetermined area and a predetermined thickness, and a supporting element configured to support the conductive adhesive while the conductive adhesive is attached to the living body; the system further including an amplifier configured to amplify a difference between signals detected by two metal electrodes selected from the at least two metal electrodes to produce an amplified signal; and a processor configured to process the amplified signal; wherein an impedance is formed between the at least two metal electrodes attached to the side of the conductive adhesive, the impedance depending on a thickness of the conductive adhesive and having a value that prevents the at least two metal electrodes from being shorted together.

In another general aspect, a method of manufacturing an electrode for measuring a bio potential includes cutting a hole in a supporting element to a conductive adhesive having a predetermined area and a predetermined thickness so that the conductive adhesive having a predetermined size is inserted; coating an adhesion material on, or attaching the adhesion material, to one side of the supporting element that contacts a living body; and inserting the conductive adhesive into the supporting element, wherein one side of the conductive adhesive is to configured to have at least two metal electrodes attached thereto, and another side of the conductive adhesive is configured to be attached to a living body while the electrode is being used; and an impedance is formed between the at least two metal electrodes while the at least two metal electrodes are attached to the side of the conductive adhesive, the impedance depending on a thickness of the conductive adhesive and having a value that prevents the at least two metal electrodes from being shorted together.

The method may further include attaching protective films to both sides of the conductive adhesive and the supporting element.

The method may further include attaching the at least two metal electrodes to the conductive adhesive; attaching at least two terminals to the conductive adhesive, the at least two terminals respectively corresponding to the at least two metal electrodes; and connecting the at least two terminals to respective ones of the at least two metal electrodes; wherein the at least two terminals may be configured to be connected to a physiological signal measuring system to connect the at least two metal electrodes to the physiological signal measuring system.

Other features and aspects will be apparent from the following detailed description, the drawings, and the claims.

DETAILED DESCRIPTION

Figure 1:
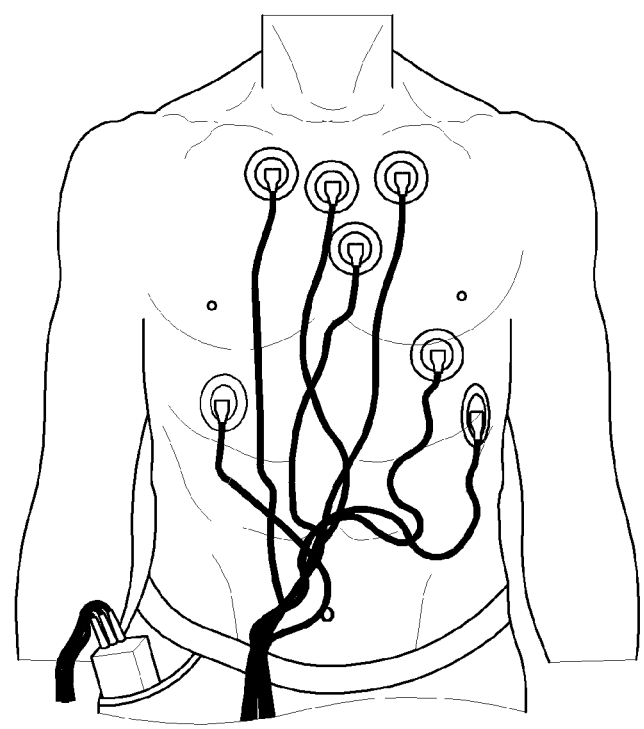
FIG. 1 illustrates an example of an electrode for a living body attached to the skin of a user, and a portable measuring system.
Figure 2:
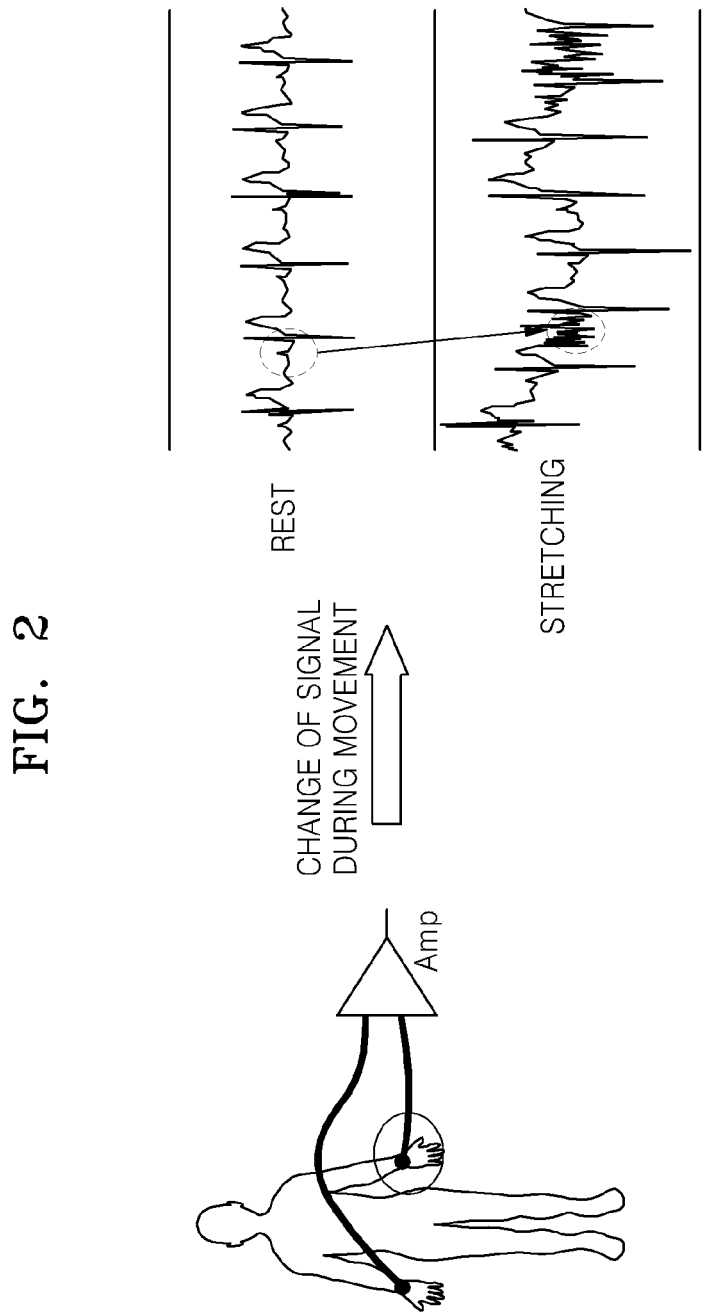
FIG. 2 illustrates an example of noise generated in a measured physiological signal due to a change in an interface caused by a movement of a body.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

An apparatus for measuring a physiological signal includes an electrode for a living body that is attached to a human body, and a sensing platform that is attached to the electrode for a living body. Generally, the electrode for a living body is formed of a conductive adhesive, an adhesive sheet that is attached to the skin of the human body, a metal electrode, and other components. A protrusion of the metal electrode electrically and mechanically connects the electrode to the sensing platform.

Figure 3:
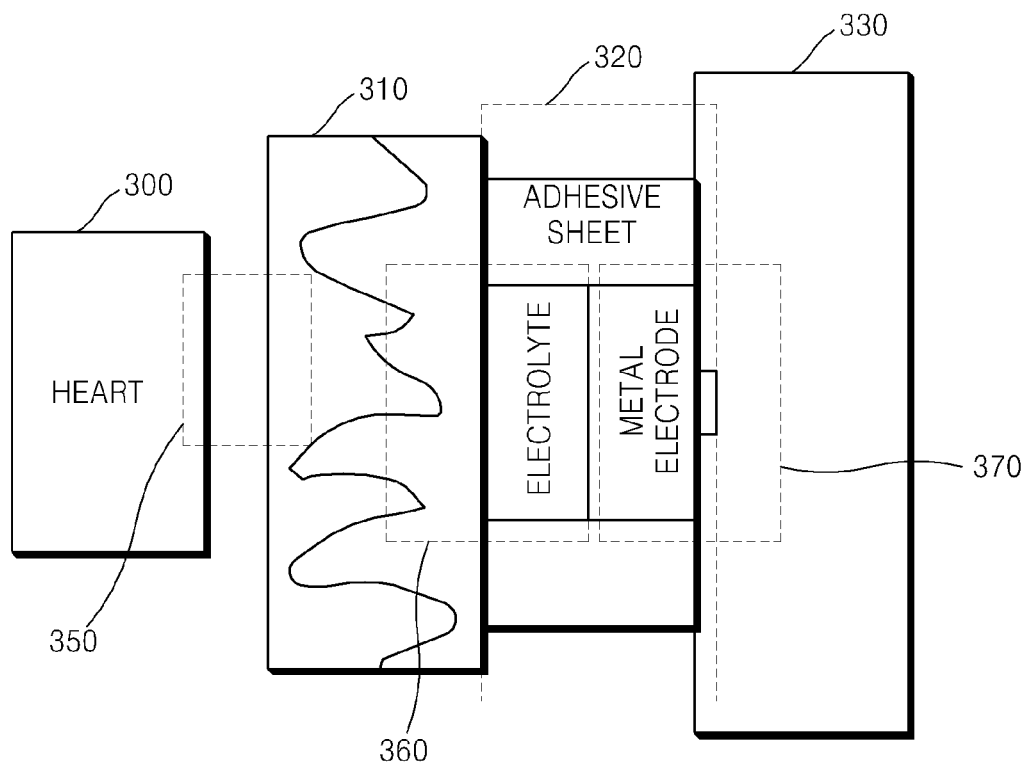
FIG. 3 illustrates an example of an interface in a channel that is used for measuring a physiological signal.

FIG. 3 illustrates an example of an interface in a channel that is used for measuring a physiological signal. Noise may be generated for a variety of reasons during physiological signal measurement, as will be described with reference to FIG. 3.

The interface in the channel includes three parts, that is, a first interface 350 between a part of a human body (for example, a heart 300) of which a physiological signal is to be measured and the skin 310 of the human body, a second interface 360 between the skin 310 and an electrode 320, and a third interface 370 between the electrode 320 and a measuring system 330.

In the first interface 350, noise is generated due to a change of an electromyogram (EMG) and axon action potential in the skin, which is caused by breathing and motion of the human body. In the second interface 360, a motion artifact is generated due to a disturbance in a charge distribution due to changes in interfaces between a metal electrode and an electrolyte, and between the electrolyte and the skin 310. A system load is transmitted to the second interface 360 through the third interface 370 between the measuring system 330 and the electrode 320.

In the structure of FIG. 3, when an exposed metal surface of the measuring system 330 is coupled one-to-one with a conductive gel of the electrode 320, a relative displacement is generated in the third interface 370 between the measuring system 330 and the electrode 320 due to an external movement, and a motion artifact is generated due to an additional change of an interface if the skin 310 expands and thus a displacement is transmitted to the electrode 320.

For example, an electrocardiogram (ECG), which is an electrical physiological signal that is generally used for diagnosing a heart disease, is used for diagnosing the heart disease (for example, an arrhythmia) based on a change in an RR interval in a period of a measured signal. When a motion artifact is generated due to a dynamic change in the circumstances illustrated in FIG. 3 and thus a physiological signal is distorted, the physiological signal may not be analyzed correctly, thereby resulting in an incorrect diagnosis.

Figure 5:
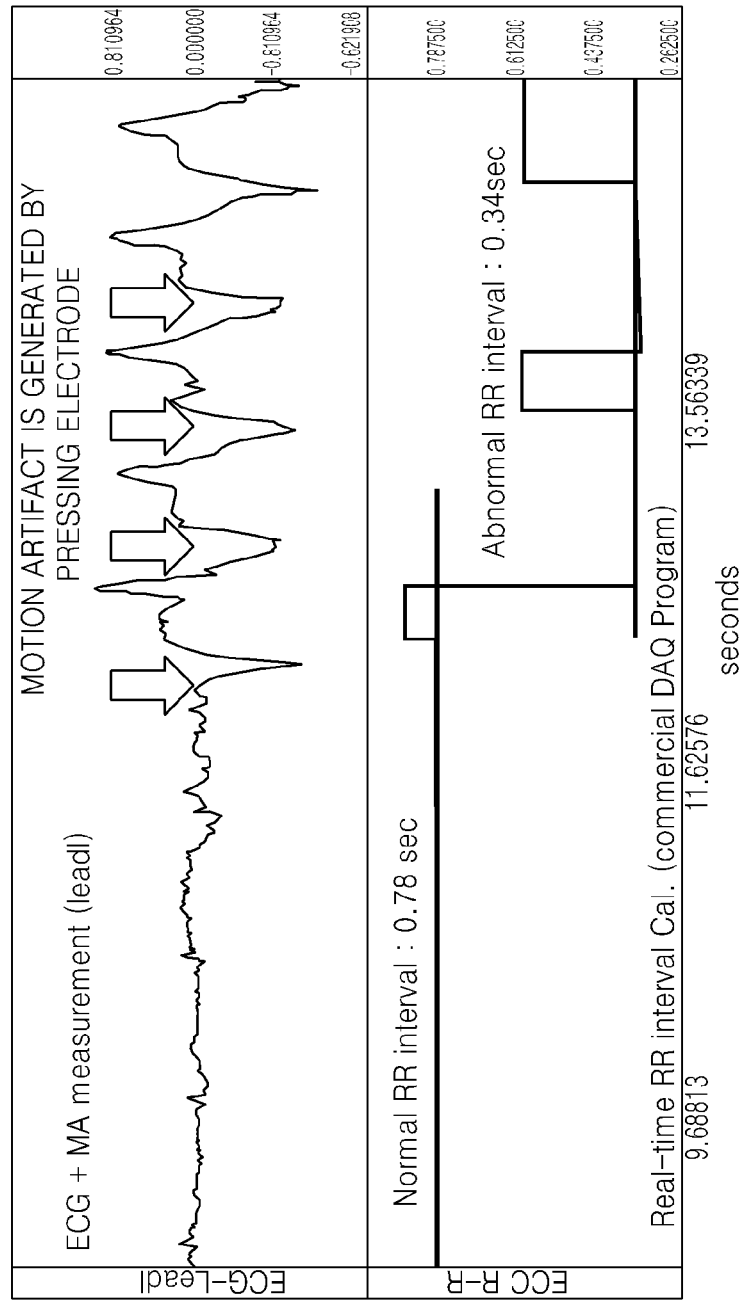
FIG. 5 illustrates examples of diagnosis parameter errors generated due to generation of a motion artifact.

FIG. 5 illustrates examples of diagnosis parameter errors generated due to generation of a motion artifact. In FIG. 5, it is shown that the RR interval changes when the motion artifact is generated by pressing an electrode.

In the conventional art, in order to eliminate noise generated due to a dynamic change in circumstances, an electrical characteristic change due to a movement of a human body is directly measured, and then a motion artifact is eliminated through signal processing based on a result of the measuring.

In examples described in this application, unlike in the conventional art, a motion artifact is minimized by implementing a bio potential measuring electrode with a structure that has a robust resistance to motion artifacts.

Figure 13:
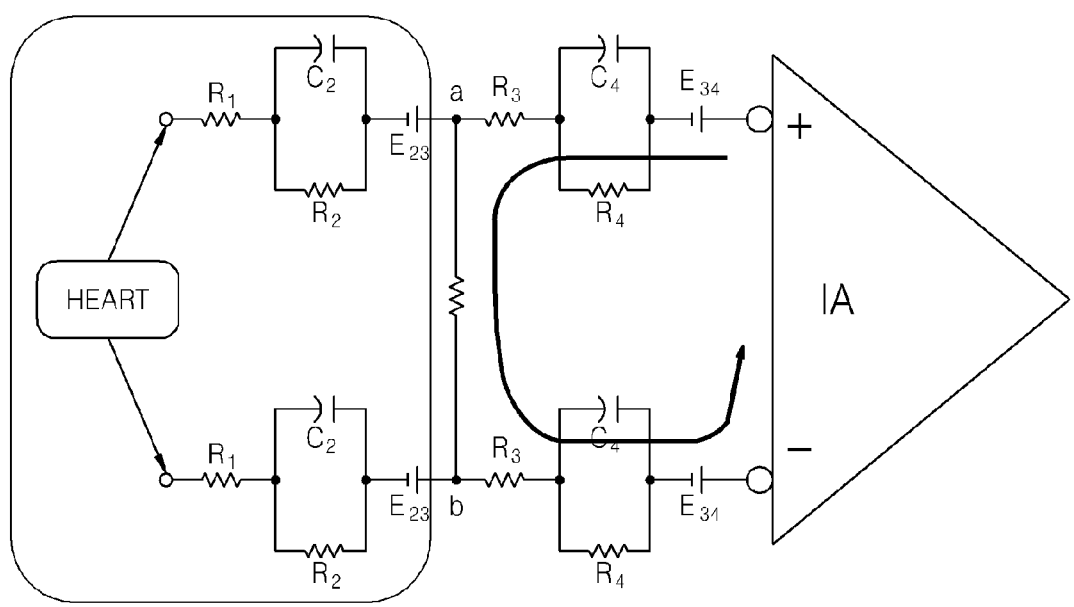
FIG. 13 illustrates an example of a circuit model when using an electrode for measuring a bio potential having a single conductive adhesive.

In the conventional art, a multi-channel electrode is formed by one-to-one connection of a plurality of metal electrodes and a plurality of conductive adhesives. However, in the examples described in this application, a multi-channel electrode is formed of a plurality of metal electrodes and a single conductive adhesive to provide a solid cohesiveness with respect to the skin of a human body, and thus a change of the interfaces is minimized. The single conductive adhesive has an effect of connecting a resistor between two terminals a and b as shown in FIG. 13, and the amplitude of a measured signal depends on the size of the connected resistor.

Figure 6:
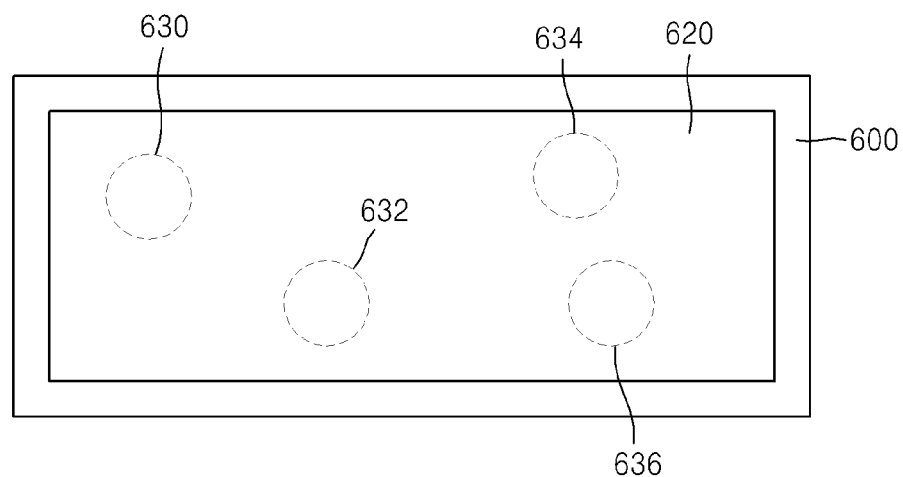
FIG. 6 is a plan view illustrating an example of a multi-channel electrode for measuring a bio potential.

FIG. 6 is a plan view illustrating an example of a multi-channel electrode for measuring a bio potential. The multi-channel electrode of FIG. 6 includes a conductive adhesive 620 and a supporting element 600. The supporting element 600 may be omitted depending on the viscosity of the conductive adhesive 620. Reference numerals 630, 632, 634, and 636 indicate locations of metal electrodes that are attached to the conductive adhesive 620. The number of metal electrodes is not limited to four, and the locations of the metal electrodes may be changed if necessary. A suitable conductive adhesive for the conductive adhesive 620 may be, for example, a conductive adhesive hydrogel that may be obtained, for example, from AmGel Technologies, Fallbrook, Calif., a division of Axelgaard Manufacturing Co., Ltd., or Katecho, Inc., Des Moines, Iowa. The conductive adhesive hydrogel may contain a mesoporous material that has an adhesive property and contains an electrolyte to provide a conductive property.

Figure 7:
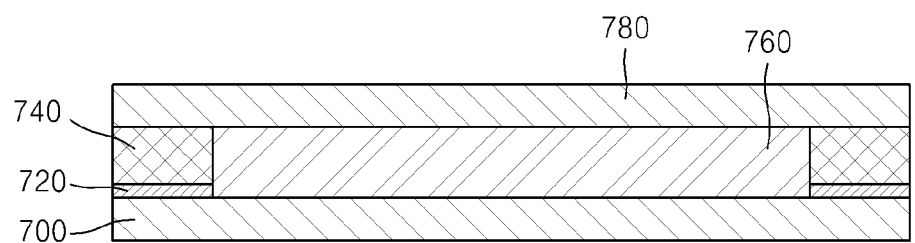
FIG. 7 is a cross-sectional view illustrating an example of a multi-channel electrode for measuring a bio potential.

FIG. 7 is a cross-sectional view illustrating an example of a multi-channel electrode for measuring a bio potential. The multi-channel electrode of FIG. 7 includes a conductive adhesive 760 and a supporting element 740, and an adhesion material 720 may be coated on the supporting element 740 to provide adhesive strength when the supporting element 740 is attached to a living body. The multi-channel electrode of FIG. 7 may further include protective films 700 and 780 to protect adhesion surfaces of the conductive adhesive 760 and the adhesion material coated 720 coated on the supporting element 740 at least until the multi-channel electrode is ready to be used, at which time the protective films 700 and 780 may be removed. The supporting element 740 and the adhesion material 720 may be omitted depending on the adhesive strength and the viscosity of the conductive adhesive 760. For example, the supporting element 700 may be omitted if the viscosity of the conductive adhesive 760 is high enough to enable the conductive adhesive 760 to maintain its shape and not shake up and down and left and right while the conductive adhesive 760 is attached to a living body, and the adhesion material 720 may be omitted if the adhesive strength of the conductive adhesive 760 is sufficiently high to keep the conductive adhesive 760 attached to a living body.

As stated above, an example of the multi-channel electrode for measuring a bio potential described in this application includes the conductive adhesive 620 or 760 and the supporting element 600 or 740.

At least two electrodes are attached to one side of the conductive adhesive 620 or 760, and the other side of the conductive adhesive 620 or 760 is attached to a living body. The conductive adhesive 620 or 760 has a predetermined area and a predetermined thickness, and is formed as a single piece.

The supporting element 600 or 740 supports the conductive adhesive 620 or 760 so that the conductive adhesive 620 or 760 cannot shake up and down and left and right while the conductive adhesive 620 or 760 is attached to a living body. The adhesion material 720 that may adhere to a living body may be coated on one side of the supporting element 600 or 740 that contacts a living body. The supporting element 600 or 740 and the adhesion material 720 may be omitted depending on the adhesive strength and the viscosity of the conductive adhesive 620 or 760.

When at least two metal electrodes are attached to the conductive adhesive 620 or 760, an impedance is formed between the at least two metal electrodes. The impedance depends on a thickness of the conductive adhesive 620 or 760, and has a value that prevents the at least two metal electrodes from being shorted together. The impedance becomes smaller as the thickness of the conductive adhesive 620 or 760 increases, and becomes larger as the thickness of the conductive adhesive 620 or 760 decreases. Accordingly, the impedance may be adjusted by adjusting the thickness of the conductive adhesive 620 or 760. An example of a suitable impedance is about 10 kΩ) or more, but this is merely one example, and other impedances may be suitable depending on the circumstances.

The impedance also depends on a distance between points where the at least two metal electrodes are located on the conductive adhesive 620 or 760, and becomes smaller as the distance decreases, and larger as the distance increases. Accordingly, the impedance may be adjusted by adjusting the distance between the points where the at least two metal electrodes are located on the conductive adhesive 620 or 760.

The impedance also depends on areas of the at least two metal electrodes, and becomes smaller as the areas increase, and larger as the areas decrease. Accordingly, the impedance may be adjusted by adjusting the areas of the at least two metal electrodes.

The impedance also depends on a composition of the conductive adhesive 620 or 760. Accordingly, the impedance may be adjusting by changing the composition of the conductive adhesive 620 or 760.

When a metal electrode (not shown in FIGS. 6 and 7, but shown, for example, in FIGS. 8 and 9) is attached to the conductive adhesive 620 or 760, or is inserted into the conductive adhesive 620 or 760, for example, at any of the locations 630, 632, 634, and 636, the metal electrode and the conductive adhesive 620 or 760 cooperate to form an electrode having a filter characteristic, such that the electrode may function as a filter for an electrical signal sensed by the electrode. For example, the filter may be a high-pass filter. The properties of the filter depend, for example, on an area of the metal electrode and a thickness of the conductive adhesive 620 or 760, and thus may be adjusted by adjusting the area of the metal electrode and/or the thickness of the conductive adhesive 620 or 760.

Protective films may be attached to both sides of the conductive adhesive 620 or 760 and the supporting element 600 or 740 to protect adhesion surfaces of the conductive adhesive 620 or 760 and the adhesion material 720 coated on the supporting element 740 at least until the multi-channel electrode is ready to be used, at which time the protective films 700 and 780 may be removed. As discussed above, FIG. 7 shows protective films 700 and 780 attached to both sides of the supporting conductive adhesive 760 and the supporting element 740.

Figure 8:
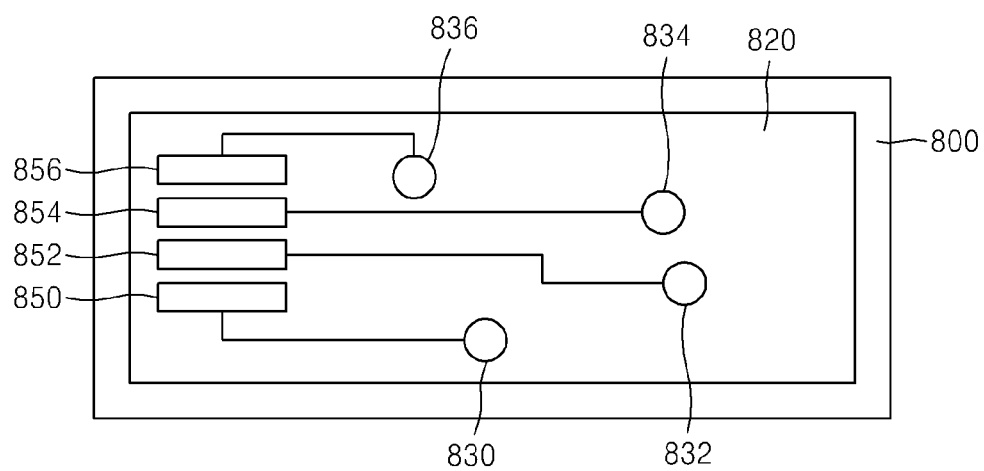
FIG. 8 is a plan view illustrating an example of a multi-channel electrode for measuring a bio potential.

FIG. 8 is a plan view illustrating an example of a multi-channel electrode for measuring a bio potential. The multi-channel electrode of FIG. 8 includes a conductive adhesive 820, a supporting element 800, and at least two metal electrodes 830, 832, 834, and 836, and at least two terminals 850, 852, 854, and 856 respectively corresponding to the at least two metal electrodes 830, 832, 834, and 836 and respectively connected to the at least two metal electrodes 830, 832, 834, and 836. Although four metal electrodes and four terminals are illustrated in FIG. 8, the number of metal electrodes and the number of terminals are not limited to four. The locations of the metal electrodes 830, 832, 834, and 836 and the terminals 850, 852, 854, and 856 on the conductive adhesive 820 may be changed if necessary. The supporting element 800 may be omitted depending on the adhesive strength and the viscosity of the conductive adhesive 820.

Figure 9:
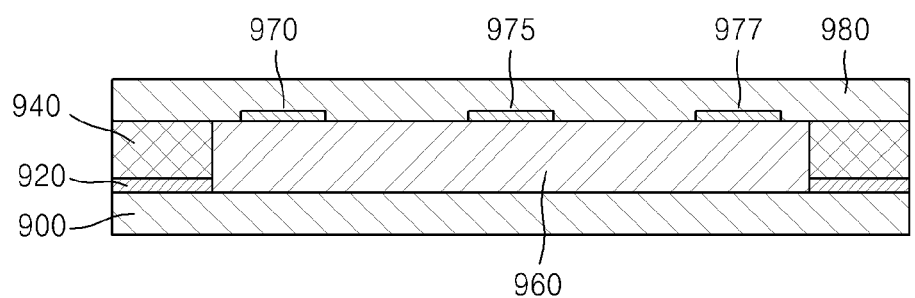
FIG. 9 is a cross-sectional view illustrating an example of a multi-channel electrode for measuring a bio potential.

FIG. 9 is a cross-sectional view illustrating an example of a multi-channel electrode for measuring a bio potential. The multi-channel electrode of FIG. 9 includes a conductive adhesive 960 and a supporting element 940, and an adhesion material 920 may be coated on the supporting element 940 to provide adhesive strength when the supporting element 940 is attached to a living body. The multi-channel electrode of FIG. 9 may further include protective films 900 and 980 to protect adhesion surfaces of the conductive adhesive 960 and the adhesion material 920 coated on the supporting element 940 at least until the multi-channel electrode is ready to be used, at which time the protective films 900 and 980 may be removed. The supporting element 940 and the adhesion material 920 may be omitted depending on the adhesive strength and the viscosity of the conductive adhesive 960.

At least two electrodes 970, 975, and 977 are attached to one side of the conductive adhesive 820 or 960, and the other side of the conductive adhesive 820 or 960 is attached to a living body. The conductive adhesive 820 or 960 has a predetermined area and a predetermined, thickness, and is formed as a single piece.

The supporting element 800 or 940 supports the conductive adhesive 820 or 960 so that the conductive adhesive 820 or 960 cannot shake up and down and left and right while the conductive adhesive 820 or 960 is attached to a living body. The adhesion material 920 adheres to a living body when the one side of the supporting element 940 on which the adhesion material 940 is coated contacts a living body. The supporting element 800 or 940 and the adhesion material 920 may be omitted depending on the adhesive strength and the viscosity of the conductive adhesive 820 or 960.

At least two metal electrodes, for example, four metal electrodes 830, 832, 834, and 836, are attached to the conductive adhesive 820, and an impedance is formed between the at least two metal electrodes 830, 832, 834, and 836. The impedance depends on a thickness of the conductive adhesive 820 or 960, and has a value that prevents the at least two metal electrodes from being shorted together. The impedance becomes smaller as the thickness of the conductive adhesive 820 or 960 increases, and becomes larger as the thickness of the conductive adhesive 820 or 960 decreases. Accordingly, the impedance may be adjusted by adjusting the thickness of the conductive adhesive 820 or 960.

The impedance also depends on a distance between points where the at least two metal electrodes are located on the conductive adhesive 820 or 960, and becomes smaller as the distance decreases, and larger as the distance increases. Accordingly, the impedance may be adjusted by adjusting the distance between the points where the at least two metal electrodes 970, 975, and 977 are located on the conductive adhesive 820 or 960.

The impedance also depends on areas of the at least two metal electrodes, and becomes smaller as the areas increase, and larger as the areas increase. Accordingly, the impedance may be adjusted by adjusting the areas of the at least two metal electrodes.

The impedance also depends on a composition of the conductive adhesive 620 or 760. Accordingly, the impedance may be adjusting by changing the composition of the conductive adhesive 620 or 760.

When a metal electrode, such as the metal electrodes 830, 832, 834, and 836, is attached to the conductive adhesive 820 or 960, or is inserted into the conductive adhesive 820 or 960, the metal electrode and the conductive adhesive 820 or 960 cooperate to form an electrode having a filter characteristic, such that the conductor may function as a filter for an electrical signal sensed by the electrode. For example, the filter may be a high-pass filter. The properties of the filter depend, for example, on an area of the metal electrode and a thickness of the conductive adhesive 820 or 960, and thus may be adjusted by adjusting the area of the metal electrode and/or the thickness of the conductive adhesive 820 or 960.

Protective films 900 and 980 may be attached to both sides of the conductive adhesive 820 or 960 and the supporting element 800 or 940 to protect adhesion surfaces of the conductive adhesive 820 or 960 and the adhesion material 920 coated on the supporting element 940 at least until the multi-channel electrode is ready to be used, at which time the protective films 900 and 980 may be removed.

The at least two metal electrodes 830, 832, 834, and 836 may be directly connected to an input channel terminal of a physiological signal measuring apparatus, or may be connected to the input channel terminal through the at least two terminals 850, 852, 854, and 856.

The at least two terminals 850, 852, 854, and 856 respectively correspond to the at least two metal electrodes 830, 832, 834, and 836, and the at least two metal electrodes 830, 832, 834, and 836 may be connected to the physiological signal measuring apparatus through the at least two terminals 850, 852, 854, and 856.

Figure 4:
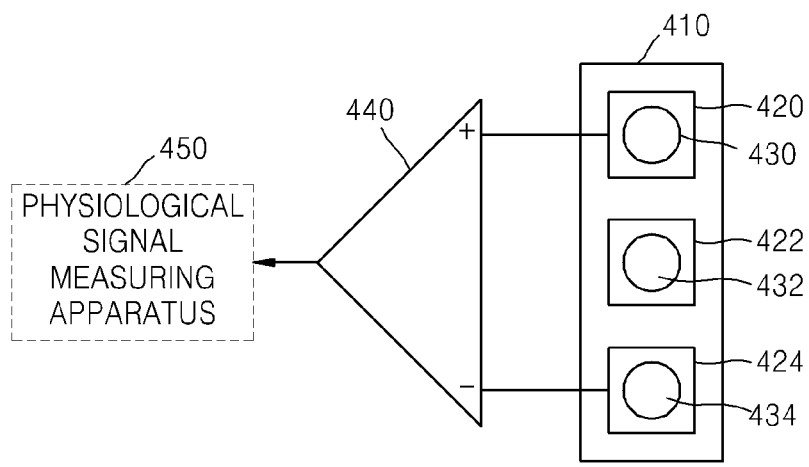
FIG. 4 illustrates an example of a conventional electrode for measuring a bio potential.

FIG. 4 illustrates an example of a conventional electrode for measuring a bio potential. In order to measure electric potentials at N points (N is a positive number) on a living body by using the conventional electrode, N metal electrodes formed of a metal such as Ag—AgCl, Au, Pt, or stainless steel and N conductive adhesives (for example, hydrogel) that are located between the N metal electrodes and the living body are necessary.

Referring to FIG. 4, in the conventional electrode, respective conductive adhesives 420, 422, and 424 are separately formed for metal electrodes 430, 432, and 434, and a supporting element 410 is required to support the conductive adhesives 420, 422, and 424. FIG. 4 illustrates a case in which three metal electrodes 430, 432, and 434 and three conductive adhesives 420, 422, and 424 are formed. A physiological signal that is received from selected ones of the metal electrodes 430, 432, and 434 (the metal electrodes 430 and 434 in the example in FIG. 4) is amplified by an amplifier 440, and the amplified physiological signal is transmitted to a physiological signal measuring apparatus 450.

On the other hand, as stated above, the electrode for measuring a bio potential according to the examples disclosed in this application includes N metal electrodes and a single conductive adhesive and thus provides a signal measurement environment that has a robust resistance to motion artifacts.

Figure 10:
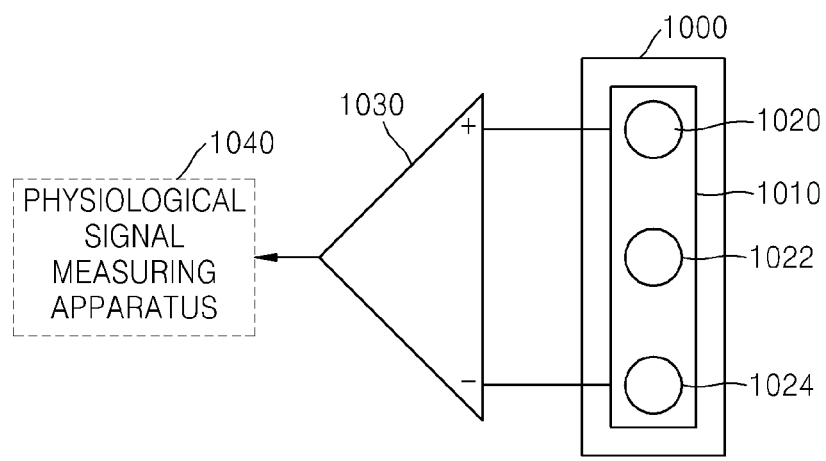
FIG. 10 illustrates an example of measuring differential signals at two different locations by using an electrode for measuring a bio potential.

FIG. 10 illustrates an example of measuring differential signals at two different locations by using an electrode for measuring a bio potential. The electrode for measuring a living body potential difference obtained from a positive (+) electrode and a negative (−) electrode is connected to a differential amplifier 1030 to form one channel. Referring to FIG. 10, respective conductive adhesives are not separately provided for three metal electrodes 1020, 1022, and 1024 as in the conventional art, but a single conductive adhesive 1010 is commonly formed for the three metal electrodes 1020, 1022, and 1024. In addition, a supporting element 1000 is provided to support the conductive adhesive 1010. A physiological signal that is received from selected ones of the metal electrodes 1020, 1022, and 1024 (the metal electrodes 1020 and 1024 in the example in FIG. 10) is amplified by an amplifier 1030, and then the amplified physiological signal is transmitted to a physiological signal measuring apparatus 1040.

Figure 11:
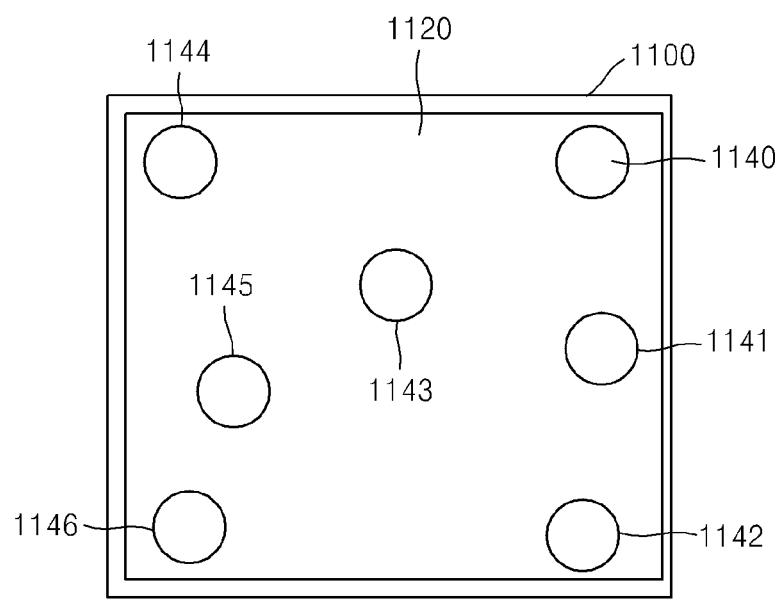
FIG. 11 illustrates an example of a multi-channel electrode including N metal pads, and illustrates an example of an electrode for measuring an electric potential difference between two locations.

FIG. 11 illustrates an example of a multi-channel electrode including N metal electrodes for measuring an electric potential difference between two locations. Seven locations 1140, 1141, 1142, 1143, 1144, 1145, and 1146 where metal electrodes may be attached are shown on a conductive adhesive 1120. A supporting element 1100 supports the conductive adhesive 1120 so that the conductive adhesive 1120 cannot shake left and right and up and down while the conductive adhesive 1120 is attached to a living body.

Figures 12A, 12B:
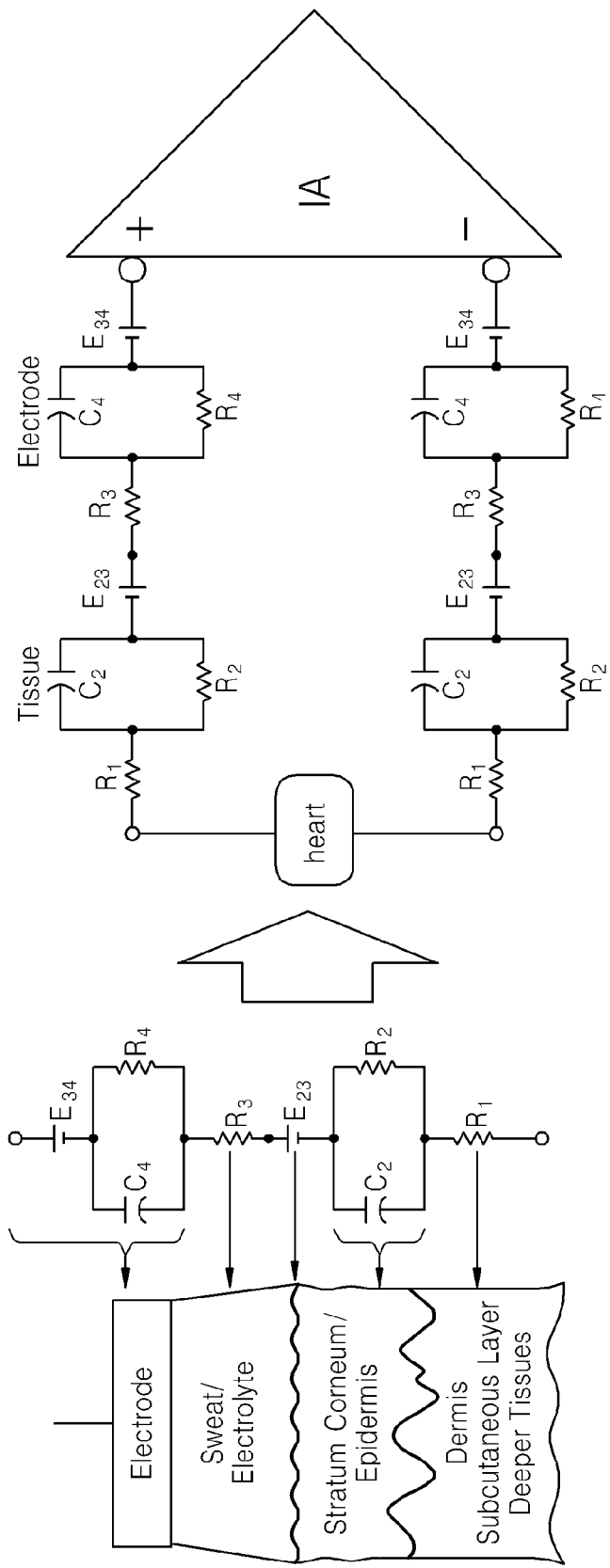
FIGS. 12A and 12B illustrate an example of a circuit model of a signal transmission path through an electrode for a living body.

FIGS. 12A and 12B illustrate an example of a circuit model of a signal transmission path through an electrode for a living body. FIG. 12A illustrates an example of a circuit model of an interface between a single electrode and a skin of a living body, and, in detail, illustrates a circuit model of an interface between an electrode for measuring a bio potential and the skin of a living body when the electrode for measuring a bio potential is attached to the skin of the living body. Each layer of the circuit model is formed of an impedance and/or a capacitance. A half cell potential $E_{23}$ is generated at an interface between a stratum corneum/epidermis layer and a sweat/electrolyte layer, and a half cell potential $E_{34}$ is generated at an interface between the sweat/electrolyte layer and the electrode. A first layer corresponding to a dermis, a subcutaneous layer, and deeper tissues is represented by an impedance R1. A second layer corresponding to the stratum corneum/epidermis layer is represented by an impedance R2 and a capacitance C2 connected in parallel. A third layer corresponding to the sweat/electrolyte layer is represented by an impedance R3. A fourth layer corresponding to the electrode is represented by an impedance R4 and a capacitance C4 connected in parallel.

FIG. 12B illustrates an example of a circuit model of a pair of electrodes and a differential signal measurement path, and, in detail, illustrates a closed loop from a signal source (for example, the heart) to a differential amplifier IA when measuring a potential difference between different points through two electrodes. A change in electrical characteristics (for example, an impedance) of a signal transmission path induced by a dynamic change when measuring a potential difference between both terminals of the signal source generates a distortion in a measured signal, and thus reduces a signal-to-noise ratio (SNR) of the measured signal.

FIG. 13 illustrates an example of a circuit model when using an electrode for measuring a bio potential having a single conductive adhesive as described above, and, in detail, illustrates a circuit model of an interface between an electrode for a living body and the skin of a living body, which is the same as the circuit model of FIG. 12B except for a connection resistor connected between two terminals a and b of signal transmission paths from a signal source (for example, a heart) to a differential amplifier IA. The connection resistor corresponds to the impedance that is formed between two metal electrodes when the two metal electrodes are attached to the conductive adhesive as described above. When the impedance value of the connection resistor is sufficiently low, two closed loops are formed, and the differential amplifier IA measures a potential difference of a closed loop adjacent to the input terminals of the differential amplifier IA, and accordingly a potential difference of the signal source (the heart) in the closed loop away from the input terminals of the differential amplifier IA cannot be measured by the differential amplifier IA. However, when the impedance value of the connection resistor is sufficiently high, only a single closed loop is formed, and the potential difference of the signal source (the heart) can be measured by the differential amplifier IA. Accordingly, by making the value of the a change in electrical characteristics of the signal transmission path may be minimized.

Figure 14:
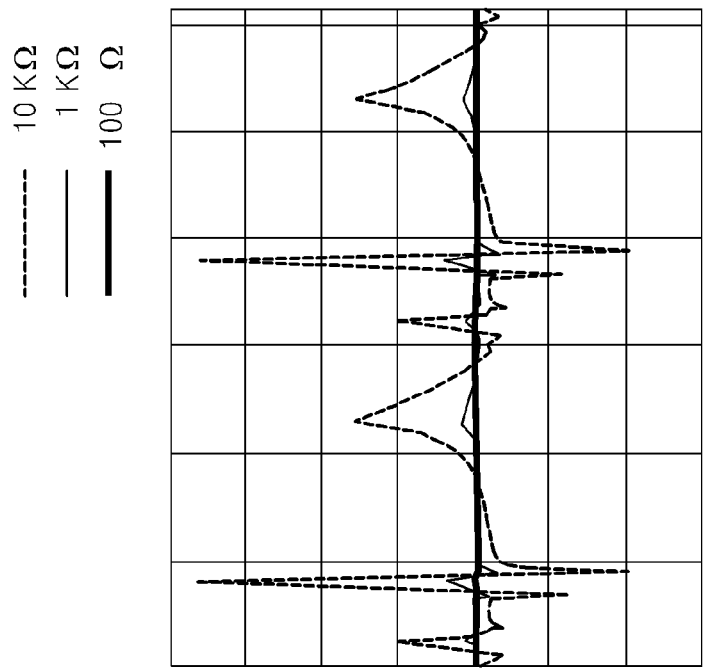
FIG. 14 is a diagram illustrating an example of a change in an amplitude of a measured physiological signal depending on the size of a connection resistor connected between signal transmission paths from signal sources to a differential amplifier in a circuit model.
Figure 14:
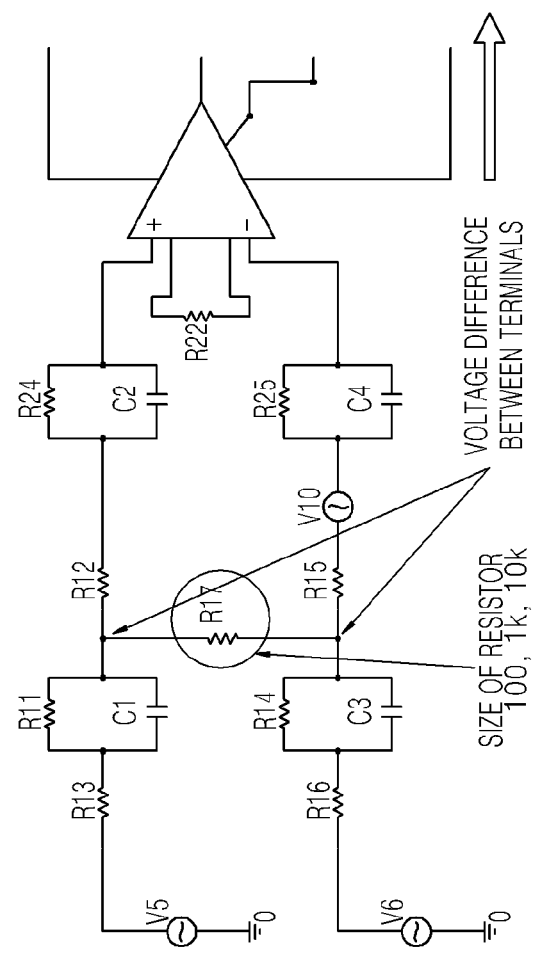

FIG. 14 is a diagram illustrating an example of a change in an amplitude of a measured physiological signal depending on the size of a connection resistor R17 connected between signal transmission paths from signal sources to a differential amplifier. Impedances R11, R12, R13, R14, R15, R16, R24, and R25 and capacitances C1, C2, C3, C4 of a circuit model in FIG. 14 respectively correspond to impedances R2, R3, R1, R2, R3, R1, C2, C3, C2, and C3 of the circuit model in FIG. 13. R22 in FIG. 14 is an additional impedance of the circuit model in FIG. 14. In FIG. 14, the connection resistor R17 is connected between signal transmission paths from two signal sources V5 and V6 to a differential amplifier, and reduces a potential difference between the terminals of the connection resistor R17, and thus reduces an amplitude of a measured physiological signal, such as an electrocardiogram (ECG) signal, corresponding to a potential difference between the signals output from the two signal sources V5 and V6. An amount by which the potential difference is reduced depends on the size of the connection resistor R17 as illustrated in a graph on the right side of FIG. 14. The graph illustrates cases in which the connection resistor R17 is 100 Ω, 1 kΩ, and 10 kΩ. An amplitude of an electrocardiogram (ECG) signal at a final output terminal of the differential amplifier in FIG. 14 can be controlled by controlling the size of the connection resistor R17. As indicated in FIG. 14, the thick solid line in the graph is a case in which the connection resistor R17 is 100 Ω, the thin solid line in the graph is a case in which the connection resistor R17 is 1 kΩ, and the dashed line in the graph is a case in which the connection resistor R17 is 10 kΩ. As can be seen from the graph, the amplitude of the ECG signal is zero when the connection resistor R17 is 100 Ω, has a very small range when the connection resistor R17 is 1 kΩ, and has a wide range with the connection resistor R17 is 10 kΩ. Thus, in the examples in FIG. 14, the best result is obtained when the connection resistor R17 is 10 kΩ.

Figure 15:
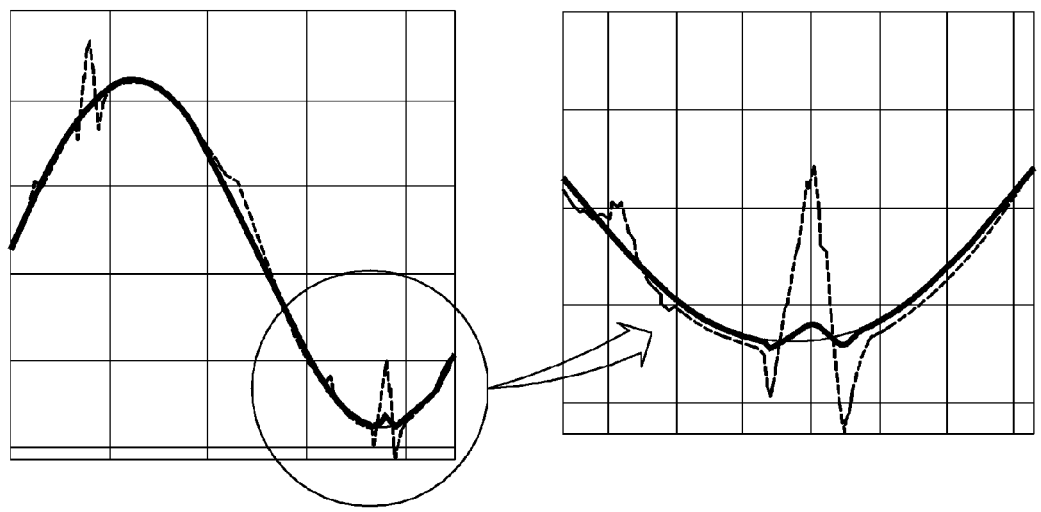
FIG. 15 illustrates an example of a signal output from a final output terminal of the circuit model illustrated in FIG. 14.

FIG. 15 illustrates an example of a signal output from a final output terminal of the circuit model illustrated in FIG. 14, i.e., a signal output from the output terminal of the differential amplifier in FIG. 14. A signal of a source V10 (representing a half cell potential change due to an external stimulus and a motion artifact) in FIG. 14 is mixed with an ECG signal in the signal output from the output terminal of the differential amplifier in FIG. 14. This mixed signal is shown in FIG. 15. Unlike the plurality of conductive adhesives used in the conventional art, the use of a single conductive adhesive as disclosed in this application may reduce a motion artifact in a measured physiological signal by minimizing a change in an interface without using an external additional sensor or signal source for measuring other physical quantities in addition to the physiological signal, and may improve a SNR of the measured physiological signal.

Figure 16:
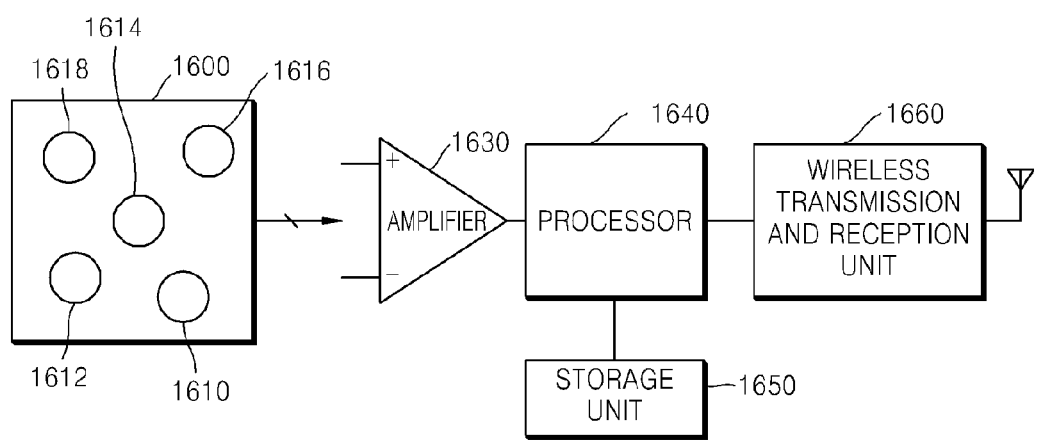
FIG. 16 illustrates an example of a physiological signal measuring system.

FIG. 16 illustrates an example of a physiological signal measuring system. The physiological signal measuring system of FIG. 16 includes an electrode 1600 for measuring a bio potential, which includes at least two metal electrodes, for example, five metal electrodes 1610, 1612, 1614, 1616, and 1618, an amplifier 1630, a processor 1640, a storage unit 1650, and a wireless transmission and reception unit 1660, although the storage unit 1650 and the wireless transmission and reception unit 1660 may be omitted.

The electrode 1600 for measuring a bio potential further includes the conductive adhesive 620 and the supporting element 600 illustrated in FIG. 6. In FIG. 16, the conductive adhesive 620 and the supporting element 600 are not shown.

As stated above with respect to FIG. 6, in the example in FIG. 16, at least two electrodes (the five metal electrodes 1610, 1612, 1614, 1616, and 1618) are attached to one side of the conductive adhesive 620, and the other side of the conductive adhesive 620 is attached to a living body. The conductive adhesive 620 has a predetermined area and a predetermined thickness, and is formed as a single piece. The supporting element 600 supports the conductive adhesive 620 so that the conductive adhesive 620 cannot shake up and down and left and right while the conductive adhesive 620 is attached to a living body. The supporting element 600 may be omitted depending on the adhesive strength and the viscosity of the conductive adhesive 620.

Referring to FIG. 16, the at least two metal electrodes 1610, 1612, 1614, 1616, and 1618 are attached to the conductive adhesive (not shown) of the electrode 1600 for measuring a bio potential. The amplifier 1630 amplifies a signal difference between two metal electrodes selected from the at least two metal electrodes 1610, 1612, 1614, 1616, and 1618. The processor 1640 processes the amplified signal produced by the amplifier 1630.

When the at least two metal electrodes 1610, 1612, 1614, 1616, and 1618 are attached to the conductive adhesive (not shown), an impedance is formed between the at least two metal electrodes 1610, 1612, 1614, 1616, and 1618. The impedance depends on a thickness of the conductive adhesive (not shown), and has a value that prevents the at least two metal electrodes 1610, 1612, 1614, 1616, and 1618 from being shorted together.

When a metal electrode of the electrode 1600 for measuring a bio potential, such as the metal electrodes 1610, 1612, 1614, 1616, and 1618, is attached to or inserted into the conductive adhesive (not shown), the metal electrode and the conductive adhesive cooperate to form an electrode having a filter characteristic, such that the conductor may function as a filter for an electrical signal sensed by the electrode. For example, the filter may be a high-pass filter. The properties of the filter depend, for example, on an area of the metal electrode and a thickness of the conductive adhesive, and thus may be adjusted by adjusting the area of the metal electrode and/or the thickness of the conductive adhesive.

The system of FIG. 16 may include more than two amplifiers. Each amplifier amplifies a signal difference between two metal electrodes selected from the metal electrodes 1610, 1612, 1614, 1616, and 1618, and multi-channel signals obtained through the more than two amplifiers are transmitted to the processor 1640. A signal selection may be performed by disposing a multiplexer on a transmission path through which the multi-channel signals are transmitted to the processor 1640. For example, electrical signals passing through two metal electrodes 1610 and 1612 may be input to a first amplifier (not shown), electrical signals passing through two metal electrodes 1612 and 1614 may be input to a second amplifier (not shown), and electrical signals passing through two metal electrodes 1616 and 1618 may be input to a third amplifier (not shown). In this manner, multi-channel signals obtained through the first through third amplifiers are transmitted to the processor 1640. A signal selection may be performed by disposing a multiplexer on a transmission path through which the multi-channel signals are transmitted to the processor 1640.

The processor 1640 processes the amplified signal received from the amplifier 1630 by executing a predetermined program, and the storage unit 1650 stores the predetermined program and processed data obtained by the processor by processing the amplified signal. The wireless transmission and reception unit 1660 wirelessly transmits the processed data to an external device, and wirelessly receives a signal from the external device.

Figure 17:
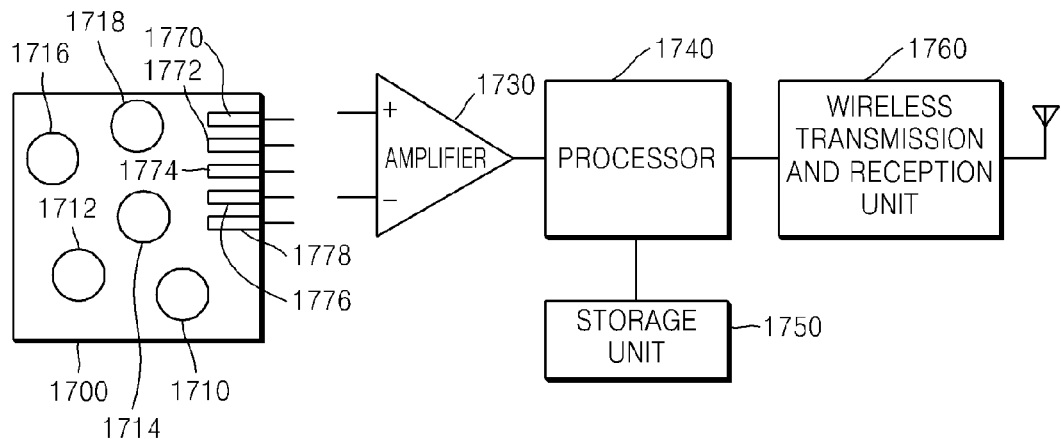
FIG. 17 illustrates an example of a physiological signal measuring system.

FIG. 17 illustrates an example of a physiological signal measuring system. The physiological signal measuring system of FIG. 17 includes an electrode 1700 for measuring a bio potential, an amplifier 1730, a processor 1740, a storage unit 1750, and a wireless transmission and reception unit 1760, although the storage unit 1750 and the wireless transmission and reception unit 1760 may be omitted.

The electrode 1700 for measuring a bio potential includes the conductive adhesive 820, the supporting element 800, and the at least two metal electrodes, for example, four metal electrodes 830, 832, 834, and 836, as illustrated in FIG. 8. In FIG. 17, the conductive adhesive 820 and the supporting element 800 are not shown, and the at least two metal electrodes 830, 832, 834, and 836 are denoted as at least two metal electrodes 1710, 1712, 1714, 1716, and 1718.

As stated above with respect to FIG. 8, the at least two metal electrodes 830, 832, 834, and 836 are attached to one side of the conductive adhesive 820, and the other side of the conductive adhesive 820 is attached to a living body.

The conductive adhesive 820 has a predetermined area and a predetermined thickness, and is formed as a single piece. The supporting element 800 supports the conductive adhesive 820 so that the conductive adhesive 820 cannot shake up and down and left and right while the conductive adhesive 820 is attached to a living body. The adhesion material 920 is coated on one side of the supporting element 800 contacts a living body, and adheres to the living body. The supporting element 800 and the adhesion material 920 may be omitted depending on the adhesive strength and the viscosity of the conductive adhesive 820.

Referring to FIG. 17, the at least two metal electrodes 1710, 1712, 1714, 1716, and 1718 are attached to the conductive adhesive 820. In addition, the at least two metal electrodes 1710, 1712, 1714, 1716, and 1718 may be directly connected to an input channel terminal of the system for measuring a physiological signal, or may be connected to the input channel terminal of the system through at least two terminals 1770, 1772, 1774, 1776, and 1778.

The at least two terminals 1770, 1772, 1774, 1776, and 1778 correspond to the at least two metal electrodes 1710, 1712, 1714, 1716, and 1718, respectively, and the at least two metal electrodes 1710, 1712, 1714, 1716, and 1718 may be connected to the physiological signal measuring system through the at least two terminals 1770, 1772, 1774, 1776, and 1778.

The amplifier 1730 amplifies a signal difference between two metal electrodes selected from the at least two metal electrodes 1710, 1712, 1714, 1716, and 1718. The processor 1740 processes the amplified signal produced by the amplifier 1730.

When a metal electrode of the electrode 1700 for measuring a bio potential, such as the metal electrodes 1710, 1712, 1714, 1716, and 1718, is attached to or inserted into the conductive adhesive (not shown), the metal electrode and the conductive adhesive cooperate to form an electrode having a filter characteristic, such that the conductor may function as a filter for an electrical signal sensed by the electrode. For example, the filter may be a high-pass filter. The properties of the filter depend, for example, on an area of the metal electrode and a thickness of the conductive adhesive, and thus may be adjusted by adjusting the area of the metal electrode and/or the thickness of the conductive adhesive.

The physiological signal measuring system of FIG. 17 may include a plurality of amplifiers. Similar to what was stated above with respect to FIG. 16, each amplifier may amplify a difference between signals input though two metal electrodes selected from the metal electrodes 1710, 1712, 1714, 1716, and 1718, and then an amplified signal is transmitted to the processor 1740.

The processor 1740 processes the amplified signal received from the amplifier 1730 by executing a predetermined program, and the storage unit 1750 stores the predetermined program and processed data obtained by the processor by processing the amplified signal. The wireless transmission and reception unit 1760 wirelessly transmits the processed data to an external device, and wirelessly receives a signal from the external device.

Figure 18:
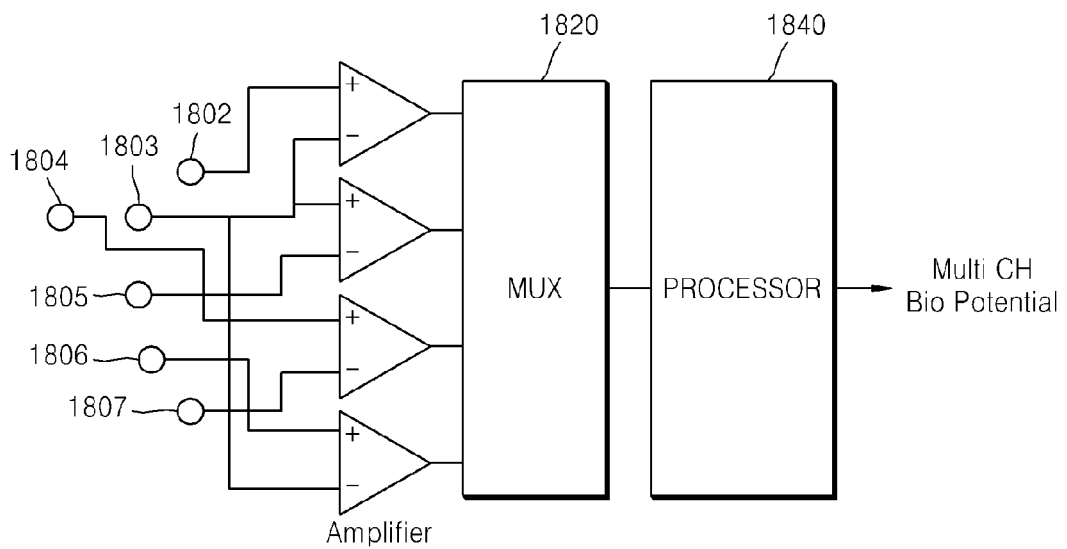
FIG. 18 is a block diagram illustrating an example of a physiological signal measuring system for outputting multi-channel physiological signals.

FIG. 18 is a block diagram illustrating an example of a physiological signal measuring system for outputting multi-channel physiological signals. Referring to FIG. 18, electrical signals passing through two arbitrary metal electrodes selected from a plurality of metal electrodes 1802, 1803, 1804, 1805, 1806, and 1807 are input to a corresponding amplifier. For example, electrical signals passing through two metal electrodes 1802 and 1803 are input to a first amplifier, electrical signals passing through two metal electrodes 1803 and 1805 are input to a second amplifier, electrical signals passing through two metal electrodes 1804 and 1807 are input to a third amplifier, and electrical signals passing through two metal electrodes 1806 and 1803 are input to a fourth amplifier. An output of each amplifier is selected by an electrode selection unit 1820, which may be a multiplexer (MUX), and an output of the electrode selection unit 1820 is processed in a processor 1840 to output multi-channel physiological signals.

Figure 19:
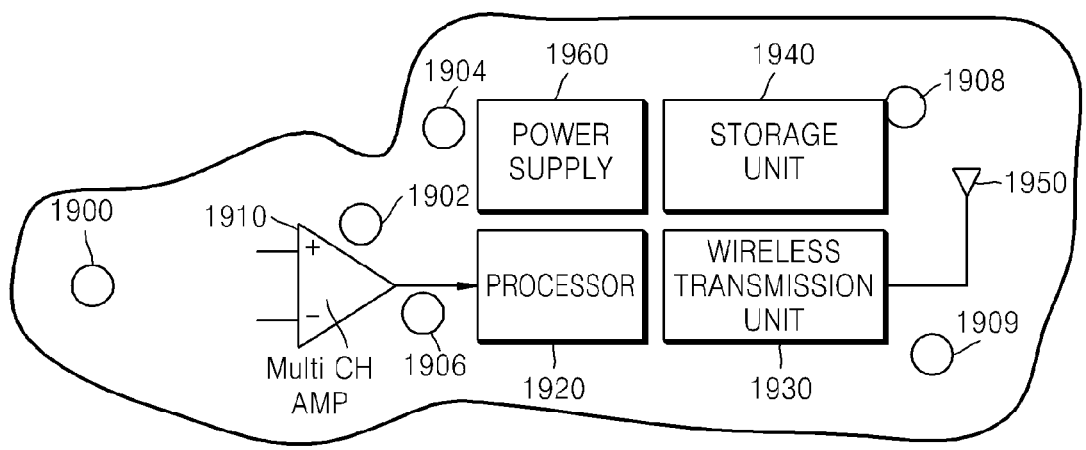
FIG. 19 is a diagram illustrating an example of a physiological signal measuring system.

FIG. 19 is a diagram illustrating an example of a physiological signal measuring system. Referring to FIG. 19, electrical signals passing through two arbitrary metal electrodes selected from a plurality of metal electrodes 1900, 1902, 1904, 1906, 1908, and 1909 attached to an electrode for measuring a bio potential are input to a differential amplifier 1910 and are amplified by the differential amplifier 1910. An amplified signal output from the differential amplifier 1910 is input to a processor 1920 and is processed by the processor 1920 using an application program selected by a user. Processed data obtained by the processor by processing the amplified signal is transmitted from the processor 1920 to a wireless transmission unit 1930, and the wireless transmission unit 1930 transmits the processed signal to the outside through an antenna 1950. The application program and the processed data is stored in a storage unit 1940, and a power supply 1960 supplies a power supply voltage to the physiological signal measuring system.

Figure 20:
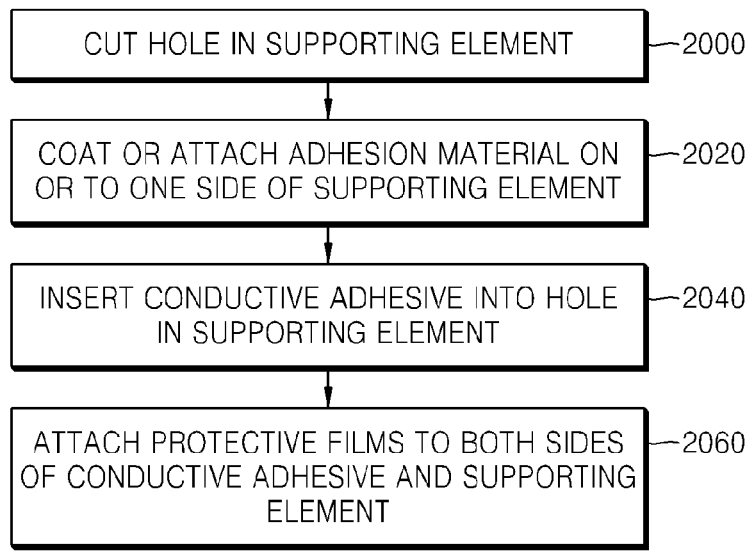
FIG. 20 is a flowchart illustrating an example of a method of manufacturing an electrode for measuring a bio potential.

FIG. 20 is a flowchart illustrating an example of a method of manufacturing an electrode for measuring a bio potential. Referring to FIG. 20, a hole is cut in a supporting element for supporting a conductive adhesive having a predetermined area and a predetermined thickness so that the conductive adhesive may be inserted into the hole (operation 2000). The size of the hole is the same size as the predetermined area of the conductive adhesive. An adhesion material is coated on or attached to one side of the supporting element that contacts a living body (operation 2020). The conductive adhesive is inserted into the hole in the supporting element (operation 2040). Finally, protective films are attached to both sides of the conductive adhesive and the supporting element to protect adhesion surfaces of the conductive adhesive and the adhesion material coated on or attached to the supporting element (operation 2060) at least until the electrode is ready to be used, at which time the protective films may be removed.

At least two metal electrodes are attached to one side of the conductive adhesive, and the other side of the conductive adhesive is attached to a living body. An impedance that is formed between the at least two metal electrodes when the at least two metal electrodes are attached to the conductive adhesive depends on the thickness of the conductive adhesive, and has a value that prevents the at least two metal electrodes from being shorted together. Accordingly, the impedance may be adjusted by adjusting the thickness of the conductive adhesive.

The method of manufacturing an electrode for measuring a bio may also include attaching at least two terminals respectively corresponding to the at least two metal electrodes to the conductive adhesive. The at least two terminals are used to connect the at least two metal electrodes to a physiological signal measuring system.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An electrode that measures a bio potential, the electrode comprising:
   at least two metal electrodes;
   a conductive adhesive having
      one side configured to have the at least two metal electrodes attached thereto while the electrode is being used, and
      another side configured to be attached to a living body while the electrode is being used, the conductive adhesive having a predetermined area and a predetermined thickness;
   a supporting element disposed at a third side of the conductive adhesive while the conductive adhesive is attached to the living body; and
   an adhesion material coated on one side of the supporting element, the supporting element and the adhesion material comprising different materials relative to one another,
   wherein
      an impedance is formed between the at least two metal electrodes while the at least two metal electrodes are attached to the side of the conductive adhesive,
      the impedance depending on a thickness of the conductive adhesive and having a value that prevents the at least two metal electrodes from being shorted together.

2. The electrode of claim 1, wherein
   the one side of the supporting element is configured to face the living body while the conductive adhesive is attached to the living body, and
   the adhesion material is configured to contact and adhere to the living body while the conductive adhesive is attached to the living body.

3. The electrode of claim 1, wherein the impedance further depends on a distance between points on the conductive adhesive where the at least two metal electrodes are attached to the conductive adhesive.

4. The electrode of claim 1, wherein the impedance further depends on areas of the at least two metal electrodes.

5. The electrode of claim 1, wherein the impedance further depends on a composition of the conductive adhesive.

6. The electrode of claim 1, further comprising a conductor configured to attach to or insert into the conductive adhesive;
   wherein the conductive adhesive and the conductor are configured to filter an electrical signal.

7. The electrode of claim 1, further comprising
   a first protective film directly attached to the one side of the conductive adhesive and the supporting element, and
   a second protective film directly attached to the other side of the conductive adhesive and the adhesion material.

8. The electrode of claim 1, wherein the adhesion material is coated on only the one side of the supporting element.

9. The electrode of claim 1, wherein the supporting element does not comprise an adhesive material.

10. The electrode of claim 1, wherein the supporting element and the adhesion material form a perimeter around the conductive adhesive.

11. An electrode that measures a bio potential, the electrode comprising:
    at least two metal electrodes;
    at least two terminals respectively corresponding to the at least two metal electrodes and respectively connected to the at least two metal electrodes;
    a conductive adhesive having one side to which the at least two metal electrodes are attached, and another side configured to be attached to a living body while the electrode is being used, the conductive adhesive having a predetermined area and a predetermined thickness;
    a supporting element disposed at a third side of the conductive adhesive while the conductive adhesive is attached to the living body; and
    an adhesion material coated on one side of the supporting element, the supporting element and the adhesion material comprising different materials relative to one another,
    wherein
       an impedance is formed between the at least two metal electrodes attached to the side of the conductive adhesive,
       the impedance depending on a thickness of the conductive adhesive and having a value that prevents the at least two metal electrodes from being shorted together.

12. The electrode of claim 11, wherein the at least two metal electrodes are configured to directly connect to a physiological signal measuring system.

13. The electrode of claim 11, wherein the at least two terminals are configured to be connected to a physiological signal measuring system to connect the at least two metal electrodes to the physiological signal measuring system.

14. The electrode of claim 11, wherein
the one side of the supporting element is configured to face the living body while the conductive adhesive is attached to the living body,
the adhesion material is configured to contact and adhere to the living body while the conductive adhesive is attached to the living body.

15. The electrode of claim 11, wherein the impedance further depends on a distance between points on the conductive adhesive where the at least two metal electrodes are attached to the conductive adhesive.

16. The electrode of claim 11, wherein the impedance further depends on areas of the at least two metal electrodes.

17. The electrode of claim 11, wherein the impedance further depends on a composition of the conductive adhesive.

18. The electrode of claim 11, further comprising a conductor configured to attach to or insert into the conductive adhesive;
wherein the conductive adhesive and the conductor are configured to filter an electrical signal.

19. A system that measures a physiological signal, the system comprising:
at least two metal electrodes;
an electrode, comprising:
a conductive adhesive having
one side to which the at least two metal electrodes are attached, and
another side configured to be attached to a living body while the electrode is being used, the conductive adhesive having a predetermined area and a predetermined thickness;
a supporting element disposed at a third side of the conductive adhesive while the conductive adhesive is attached to the living body; and
an adhesion material coated on one side of the supporting element, the supporting element and the adhesion material comprising different materials relative to one another;
an amplifier configured to amplify a difference between signals detected by two metal electrodes selected from the at least two metal electrodes to produce an amplified signal; and
a processor configured to process the amplified signal;
wherein
an impedance is formed between the at least two metal electrodes attached to the side of the conductive adhesive,
the impedance depending on a thickness of the conductive adhesive and having a value that prevents the at least two metal electrodes from being shorted together.

20. The system of claim 19, further comprising a conductor configured to attach to or insert into the conductive adhesive;
wherein the conductive adhesive and the conductor are configured to filter an electrical signal.

21. The system of claim 19, further comprising a metal electrode selection unit configured to select the two metal electrodes from the at least two metal electrodes.

22. The system of claim 19, wherein the processor is further configured to process the amplified signal to obtain processed data by executing a predetermined program; and
the system further comprises:
a storage unit configured to store the predetermined program and the processed data; and
a wireless transmission and reception unit configured to transmit the processed data to an external device.

23. A system that measures a physiological signal, the system comprising:
an electrode, comprising:
at least two metal electrodes;
at least two terminals respectively corresponding to the at least two metal electrodes and respectively connected to the at least two metal electrodes;
a conductive adhesive having
one side to which the at least two metal electrodes are attached, and
another side configured to be attached to a living body while the electrode is being used, the conductive adhesive having a predetermined area and a predetermined thickness;
a supporting element disposed at a third side of the conductive adhesive while the conductive adhesive is attached to the living body; and
an adhesion material coated on one side of the supporting element, the supporting element and the adhesion material comprising different materials relative to one another;
an amplifier configured to amplify a difference between signals detected by two metal electrodes selected from the at least two metal electrodes to produce an amplified signal; and
a processor configured to process the amplified signal;
wherein
an impedance is formed between the at least two metal electrodes attached to the side of the conductive adhesive,
the impedance depending on a thickness of the conductive adhesive and having a value that prevents the at least two metal electrodes from being shorted together.

24. The system of claim 23, further comprising a conductor configured to attach to or insert into the conductive adhesive;
wherein the conductive adhesive and the conductor are configured to filter an electrical signal.

25. The system of claim 23, further comprising a metal electrode selection unit configured to select the two metal electrodes from the at least two metal electrodes.

26. The system of claim 23, wherein the processor is further configured to process the amplified signal to obtain processed data by executing a predetermined program; and
the system further comprises:
a storage unit configured to store the predetermined program and the processed data; and
a wireless transmission and reception unit configured to transmit the processed data to an external device.

* * * * *